(12) United States Patent
Nakamura et al.

(10) Patent No.: US 9,259,485 B2
(45) Date of Patent: *Feb. 16, 2016

(54) KIDNEY-IMAGING AGENT COMPRISING RECOMBINANT GELATIN

(75) Inventors: Kentaro Nakamura, Ashigarakami-gun (JP); Yasuhiko Tabata, Uji (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/387,632

(22) PCT Filed: Jul. 30, 2010

(86) PCT No.: PCT/JP2010/062887
§ 371 (c)(1),
(2), (4) Date: Jan. 27, 2012

(87) PCT Pub. No.: WO2011/013792
PCT Pub. Date: Feb. 3, 2011

(65) Prior Publication Data
US 2012/0195828 A1  Aug. 2, 2012

(30) Foreign Application Priority Data
Jul. 30, 2009  (JP) ................. 2009-177583

(51) Int. Cl.
*A61K 49/00* (2006.01)
*A61K 51/08* (2006.01)
*C07K 14/78* (2006.01)

(52) U.S. Cl.
CPC ........... *A61K 49/0002* (2013.01); *A61K 51/082* (2013.01); *A61K 51/088* (2013.01); *C07K 14/78* (2013.01)

(58) Field of Classification Search
None
See application file for complete search history.

(56) References Cited

U.S. PATENT DOCUMENTS

| | | | |
|---|---|---|---|
| 6,992,172 B1 | 1/2006 | Chang et al. | |
| 2007/0178066 A1 | 8/2007 | Hall et al. | |
| 2010/0015044 A1 | 1/2010 | Qiu et al. | |
| 2010/0048481 A1 | 2/2010 | Bouwstra et al. | |

FOREIGN PATENT DOCUMENTS

| | | | |
|---|---|---|---|
| JP | 2009-503115 A | 1/2009 | |
| JP | 2009-023929 A | 2/2009 | |
| WO | 2006/061650 A2 | 6/2006 | |
| WO | 2007/019376 A2 | 2/2007 | |
| WO | 2007/019376 A3 | 2/2007 | |
| WO | 2007/092447 A2 | 8/2007 | |
| WO | 2008/103041 A1 | 8/2008 | |
| WO | 2008/103042 A1 | 8/2008 | |
| WO | WO 2008103046 A1 * | 8/2008 | |
| WO | 2009/040811 A2 | 4/2009 | |

OTHER PUBLICATIONS

Hwang et al. Tumor targetability and antitumor effect of docetaxel-loaded hydrophobically modified glycol chitosan nanoparticles. 2008 J. Control. Release 128: 23-31.*
Extended Search Report issued in European Patent Application No. 10804538.6 on Jan. 9, 2013.
Peter Caravan et al., "Collagen-Targeted MRI Contrast Agent for Molecular Imaging of Fibrosis", Angew. Chem. Int. Ed., 2007, 46: 8171-8173.
Yohei Ikezumi, "Role of Immunosuppressive Drugs in Chronic Glomerulonephritis", Luncheon Seminar at the 42$^{nd}$ Annual Meeting of the Japanese Society for Pediatric Nephrology, Nephrology Frontier, 2007, 6(3): 355-361 (with English translation).
Yohei Ikezumi, "Macrophage Activation Inhibitory Effect of Mizoribine in Multiple Drug Therapy of IgA Nephropathy", The 3$^{rd}$ Symposium of Japanese Study Group of Multiple Drug Therapy for IgA Nephropathy, 2008, 16(1): 115-123 (with English translation).
International Preliminary Report on Patentability and Written Opinion mailed Feb. 16, 2012, in PCT/JP2010/062887.
International Search Report mailed Sep. 28, 2010, in PCT/JP2010/062887.
JECFA Roma, Toxicological Evaluation of Certain Food Additives: WHO Food Additive Series, 1980, No. 15.
Haruhiko Kamada et al., "Synthesis of a poly(vinylpyrrolidone-co-dimethyl maleic anhydride) co-polymer and its application for renal drug targeting", Nature Biotechnology, 2003, 21: 399-404.
G. Ostgaard et al., "Lymphatic transport and organ uptake of gelatin and hyaluronan injected into the rat mesentery", Acta Physiol Scand, 1995, 153: 51-60.
Yasuhiko Tabata et al., "Macrophage activation through phagocytosis of muramyl dipeptide encapsulated in gelatin microspheres", J. Pharm. Pharmacol., 1987, 39: 698-704.
Yasuhiko Tabata et al., "Macrophage phagocytosis of biodegradable microspheres composed of L-lactic acid/glycolic acid homo- and copolymers", Journal of Biomedical Materials Research, 1988, 22: 837-858.
Yasuhiko Tabata et al., "Potentiation of Antitumor Activity of Macrophages by Recombinant Interferon Alpha A/D Contained in Gelatin Microspheres", Jpn. J. Cancer Res., 1988, 79: 636-646.
Yasuhiko Tabata et al., "Synthesis of Gelatin Microspheres Containing Interferon", Pharmaceutical Research, 1989, 6(5): 422-427.
Kenichi Shikata et al., "Diabetes Mellitus and Nephropathy—Recent Development Thereof", Diabetes Frontier, 2000, 11(5): 677-684 (with English translation).
Office Action issued in counterpart Japanese Patent Application No. 2011-524849, dated Jan. 28, 2014.
Japanese Official Action, dated Oct. 7, 2014, issued in corresponding Japanese Patent Application No. 2011-524849.

* cited by examiner

*Primary Examiner* — Michael G Hartley
*Assistant Examiner* — Jennifer Lamberski
(74) *Attorney, Agent, or Firm* — Sughrue Mion, PLLC

(57) ABSTRACT

An object of the present invention is to provide a kidney-imaging agent which is composed of bioabsorbable materials, transiently accumulates in a kidney for a short period of time, and does not remain in the kidney for a prolonged time after accumulation. The present invention provides a kidney-imaging agent which comprises a gelatin-like protein.

12 Claims, 8 Drawing Sheets

$^{125}$I-labeling of R-Gel

Biopersistence of R-Gel

R-Gel Blood Clearance

Changes in pathological conditions of the kidney of UUO model: MT-stained tissue section Accumulation of the anti-Mac1 antibody in the nephritic kidney of UUO model Kidney tissue section showing the onset of glomerulonephritis in 16-week-old HIGA mouse subjected to unilateral nephrectomy (HE staining and MT staining)

Tissue section showing pathological conditions of renal disorder in I/R model

Accumulation of R-Gel in the I/R kidney

Incorporation of R-Gel by tubular epithelial cells: Confocal laser microscopic image
*: R-Gel localization in cells is confirmed by comparing and superimposing the fluorescence image and the visible light image (transmitted light image).

Green color: Cy2-R-Gel
Transparent granular substance: Peritoneal Mφ cell

KIDNEY-IMAGING AGENT COMPRISING RECOMBINANT GELATIN

CROSS REFERENCE TO RELATED APPLICATIONS

This application is a National Stage of International Application No. PCT/JP2010/062887, filed on Jul. 30, 2010, which claims priority from Japanese Patent Application No. 2009-177583 filed on Jul. 30, 2009, the contents of all of which are incorporated herein by reference in their entirety.

TECHNICAL FIELD

The present invention relates to a kidney-imaging agent comprising a recombinant gelatin.

BACKGROUND ART

Kidney is an organ that filters waste products and excess water from blood to generate urine so as to maintain homeostasis of body fluid (extracellular fluid) and excrete protein metabolites such as urea. In addition, the kidney is responsible for regulation of endocrine secretion and metabolism such as vitamin D activation, erythropoietin production or renin production. Therefore, the kidney is known as a very important organ for the living body.

Examples of kidney diseases include acute glomerulonephritis, chronic glomerulonephritis, nephrotic syndrome, pyelonephritis, hypertensive nephrosclerosis, diabetic glomerulosclerosis, nephrolithiasis, amyloid nephropathy, renal vein thrombosis, Alport syndrome, and renal tumor. The kidney is an organ having a complex structure. In general, deterioration of renal function is irreversible except for some acute diseases. In addition, renal diseases progress as predicted, eventually resulting in "chronic renal failure." As a result of symptomatic progression, dialysis becomes required. In the case of dialysis, patients must continuously receive dialysis for 4 to 6 hours a day two or three times per week through life. Therefore, the QOL of patients is remarkably impaired. At the same time, the medical cost required for dialysis is extremely expensive (¥1,300,000,000,000), causing an enormous burden on the total medical expense in Japan (¥33,000,000,000,000). This has been problematic.

To date, a variety of drug therapies have been performed for various renal diseases. For example, drug therapies for glomerulonephritis include administration of corticosteroids for suppression of inflammatory reaction and an immunosuppressive therapy. In addition, in the case of renal cell cancer that is a major kidney cancer, stent placement and a drug therapy using molecular target drugs such as Nexavar (Sorafenib) have been conducted, in addition to surgical resection. The term "renal cell cancer" used herein refers to adenocarcinoma formed through malignant alteration of renal tubular epithelial cells in the kidney. However, satisfactory drug treatment still has not been realized in clinical practice because such drug therapies are problematic in terms of levels of side effects upon non-kidney organs, efficacy, and the like.

Meanwhile, drug delivery systems (DDSs) that allow efficient distribution of drugs to target organs have been actively studied and developed for practical use in recent years. For instance, a method using drug-carrying vesicles such as liposomes, emulsions, lipid microspheres, and nanoparticles, improved stability of PEG-modified drugs or drug carriers in blood, active targeting with the use of antibodies, and the like are suggested.

However, there are various problems relating to the drug delivery system using these techniques. It has been difficult to achieve effective delivery of drugs to kidney lesions in particular. For example, when drug-carrying vesicles are used, drug-carrying vesicles are likely to be captured in the liver, spleen, or the like, making it difficult to achieve targeting of even a normal kidney. Further, it is very difficult to perform separate targeting of normal kidney tissue and affected kidney tissue.

In particular, it is known that very large amounts of drugs pass through the kidney because of the large blood flow volume of the kidney (0.8 to 1.2 liters/minute corresponding to 20% to 25% of the cardiac output for adults). However, in spite of such large amounts of drugs passing through the kidney, substantial amounts of drugs are not transferred to kidney functional units but are excreted in urine. Therefore, sufficient drug efficacy has not been exhibited in the kidney. In addition, substantially no drug carriers capable of delivering a drug targeting a kidney or kidney functional units have been available. There are a very small number of reports on effective drug carriers capable of aiding drug targeting. One example of such drug carriers is a polyvinylpyrrolidone compound (Nature Biotechnology 21, 399-404 (2003) Synthesis of a poly(vinylpyrrolidone-co-dimethyl maleic anhydride) co-polymer and its application for renal drug targeting). However, polyvinylpyrrolidone is known as a non-bioabsorbable material that can never be degraded or metabolized in vivo (JECFA Roma, 24 Mar.-2 Apr. 1980: Toxicological Evaluation of Certain Food Additives: WHO Food Additive Series No. 15). The above compound is designed to prevent filtration/excretion through the kidney. Therefore, in order to achieve drug accumulation in the kidney, a foreign substance which is a non-bioabsorbable material needs to remain in the kidney for long time. This is significantly problematic. For such reason, it is actually difficult to use the compound in practice. In particular, the long-term retention of the compound in the kidney would increase the risk of unexpected drug-induced nephrotoxic side effects. It is known that many drugs and contrast agents cause nephrotoxic side effects. Specifically, it is important for kidney-targeting carriers to be transferred to kidney functional units immediately after being administered while having transient accumulation effects. After administration, it is desirable for kidney-targeting carriers to be removed from the kidney in an adequate manner by degradation/metabolism/excretion. For example, it is desirable for contrast agents, PET diagnostic agents (radioisotope diagnostic agents) and the like to be accumulated in 1 or 2 hours after administration and is then removed as soon as possible. However, in the above case, it was found that the polyvinylpyrrolidone compound continuously remains in the kidney at high concentrations for several days or longer. It has been impossible to solve this issue. Further, it is impossible for the above polyvinylpyrrolidone compound to achieve separate targeting of normal kidney tissue and affected kidney tissue. Therefore, the long-term retention of the compound in a normal kidney would inevitably increase the risk of unexpected drug-induced nephrotoxic side effects. Therefore, it has been problematic that the compound cannot be used in practice as an agent targeting an affected kidney.

In addition, many imaging agents/in vivo diagnostic drugs have no selectivity to distinguish between a normal kidney and an affected kidney, which has been problematic. PET (positron emission tomography) diagnosis of legions with the use of FDG (fluorodeoxyglucose) has been employed for tumor or inflammation diagnosis. However, non-specific physiological accumulation of FDG results in accumulation of FDG in a normal kidney/urinary duct. This causes an increase in the background level, making it difficult to make a diagnosis of a legion formed in a kidney or urinary duct. Also for in vivo diagnostic drugs, imaging agents capable of separately targeting normal kidney tissue and affected kidney tissue have been awaited.

That is, a targeting agent that separately targets a normal kidney and an affected kidney while having transient accumulation effects has been strongly demanded as a kidney-imaging agent. Meanwhile, for example, in the case of IgA nephropathy diagnosis, there is a report on a composition comprising an anti-IgA antibody (JP Patent Publication (Kohyo) No. 2009-503115 A). However, this composition which is provided in this document is composed of an antibody. Therefore, such composition merely acts on limited diseases (e.g., only IgA nephropathy in the case of the anti-IgA antibody described in the document). Therefore, the composition obviously lacks versatility and thus it is also not useful in practice as a diagnostic agent. That is, a versatile targeting agent capable of targeting a kidney in which a wide range of diseases are developed has been awaited.

On the other hand, biopolymers such as gelatin have been widely used as medical materials. However, it has been unknown that biopolymers can be used for targeting of an affected kidney. In addition, along with the recent development of genetic engineering techniques, protein synthesis has been conducted via gene introduction into *Escherichia coli* or yeast. With the use of this technique, a variety of recombinant collagen-like proteins have been synthesized (e.g., U.S. Pat. No. 6,992,172; and WO2008/103041). Such proteins are superior to natural gelatin in terms of non-infectious properties and homogeneity. In addition, since the sequences of the proteins have been determined, the proteins are advantageous in that they can be precisely designed in terms of strength and degradability. However, the above suggestion is limited to the use of the proteins as a substitute of natural gelatin. Needless to say, it has been unknown that they can be used as targeting agents for an affected kidney.

PRIOR ART DOCUMENTS

Non-Patent Documents

Non-Patent Document 1: Nature Biotechnology 21, 399-404 (2003)
Non-Patent Document 2: JECFA Roma, 24 Mar.-2 Apr. 1980: Toxicological Evaluation of Certain Food Additives: WHO Food Additive Series No. 15

Patent Documents

Patent Document 1: JP Patent Publication (Kohyo) No. 2009-503115 A
Patent Document 2: U.S. Pat. No. 6,992,172
Patent Document 3: WO2008/103041

SUMMARY OF INVENTION

Object to be Solved by the Invention

An object to be solved by the present invention is to provide a kidney-imaging agent which is composed of bioabsorbable materials, transiently accumulates in a kidney for a short period of time, and does not remain in the kidney for a prolonged time after accumulation. Another object to be solved by the present invention is to provide a kidney-imaging agent that widely accumulates in an affected kidney and shows a different level of accumulation in a normal kidney and an affected kidney.

Means for Solving the Object

As a result of intensive studies to achieve the above objects, the present inventors found that a gelatin-like protein such as a recombinant gelatin having an amino acid sequence derived from a partial amino acid sequence of collagen accumulates in a kidney. Further, the present inventors found that a kidney-imaging agent can be provided with the use of such accumulation effects in a kidney. This has led to the completion of the present invention.

The present invention provides a kidney-imaging agent which comprises a gelatin-like protein.

Preferably, the gelatin-like protein is gelatin, collagen, fibronectin, pronectin, vitronectin, or a combination thereof.

Preferably, the gelatin-like protein is a recombinant gelatin having an amino acid sequence derived from a partial amino acid of collagen.

Preferably, the recombinant gelatin comprises repeats of a sequence represented by Gly-X-Y characteristic to collagen and has a molecular weight of 2 KDa to 100 KDa. wherein X and Y each independently represent an amino acid and a plurality of Gly-X-Y sequences may be the same or different.

Preferably, the recombinant gelatin comprises repeats of a sequence represented by Gly-X-Y characteristic to collagen and has a molecular weight of 10 KDa to 90 KDa. wherein X and Y each independently represent an amino acid and a plurality of Gly-X-Y sequences may be the same or different.

Preferably, the recombinant gelatin comprises repeats of a sequence represented by Gly-X-Y characteristic to collagen and has two or more sequences of cell adhesion signals in a single molecule wherein X and Y each independently represent an amino acid and a plurality of Gly-X-Y sequences may be the same or different.

Preferably, the cell adhesion signal sequence is an amino acid sequence represented by Arg-Gly-Asp.

Preferably, the amino acid sequence of the recombinant gelatin does not comprise any of serine and threonine.

Preferably, the amino acid sequence of the recombinant gelatin does not comprise any of serine, threonine, asparagine, tyrosine, and cysteine.

Preferably, the amino acid sequence of the recombinant gelatin does not comprise an amino acid sequence represented by Asp-Arg-Gly-Asp (SEQ ID NO: 2).

Preferably, the recombinant gelatin is represented by the following formula:

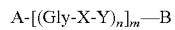

wherein A represents any amino acid or amino acid sequence, B represents any amino acid or amino acid sequence, there exist n amino acids each independently represented by X, there exist n amino acids each independently represented by Y, n represents an integer from 3 to 100, m represents an integer of 2 to 10, and n Gly-X-Y sequences may be the same or different.

Preferably, the recombinant gelatin is represented by the following formula:

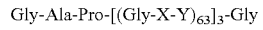

wherein there exist 63 amino acids each independently represented by X, there exist 63 amino acids each independently represented by Y, and n Gly-X-Y sequences may be the same or different.

Preferably, the recombinant gelatin has the following (1) or (2):
(1) the amino acid sequence shown in SEQ ID NO: 1; or
(2) an amino acid sequence having 80% or more homology to the amino acid sequence shown in SEQ ID NO: 1 and having an action to accumulate in kidney.

Preferably, the recombinant gelatin is crosslinked.

Preferably, the crosslinking is carried out using an aldehyde, condensing agent, heat crosslinking, photo crosslinking or enzyme.

Preferably, the kidney-imaging agent of the present invention further comprises a labeled probe.

Preferably, the labeled probe is a fluorescent dye, a radioisotope, a nuclide used for PET, a nuclide used for SPECT, an MRI contrast medium, a CT contrast medium, or a magnetic material.

Preferably, the fluorescent dye is a quantum dot, indocyanine green, or a near-infrared fluorescent dye; each of the radioisotope, the nuclide used for PET, and the nuclide used for SPECT is $^{11}C$, $^{13}N$, $^{15}O$, $^{18}F$, $^{66}Ga$, $^{67}Ga$, $^{68}Ga$, $^{60}Cu$, $^{61}Cu$, $^{62}Cu$, $^{67}Cu$, $^{64}Cu$, $^{48}V$, Tc-99m, $^{241}Am$, $^{55}Co$, $^{57}Co$, $^{153}Gd$, $^{111}In$, $^{133}Ba$, $^{82}Rb$, $^{139}Ce$, Te-123m, $^{137}Cs$, $^{86}Y$, $^{90}Y$, $^{185/187}Re$, $^{186/188}Re$, $^{125}I$, or a complex thereof, or a combination thereof; and each of the MRI contrast medium, the CT contrast medium, and the magnetic material is gadolinium, Gd-DTPA, Gd-DTPA-BMA, Gd-HP-DO3A, iodine, iron, iron oxide, chromium, manganese, a complex or chelate complex thereof, or a combination thereof.

Preferably, the gelatin-like protein and the labeled probe are physically or chemically bound directly or via a linker.

Preferably, the bond is a coordinate bond, a covalent bond, a hydrogen bond, a hydrophobic interaction, or a physical adsorption.

Preferably, the kidney is a kidney affected with a disease.

Preferably, the disease is glomerulonephritis, IgA nephropathy, diabetic nephropathy, membranous nephropathy, hydronephrosis, contrast nephropathy, pyelonephritis, renal failure, acute nephritis, chronic nephritis, interstitial nephritis, renal disorder, nephrotic syndrome, hypertensive nephrosclerosis, diabetic glomerulosclerosis, nephrolithiasis, amyloid nephropathy, renal vein thrombosis, Alport syndrome, or renal tumor.

The present invention further provides a method for imaging a kidney, which comprises administering a gelatin-like protein to a subject.

The present invention further provides use of a gelatin-like protein for production of a kidney-imaging agent.

Effect of the Invention

Imaging of kidney can be achieved with the use of the kidney-imaging agent of the present invention by making use of its accumulation effects in the kidney. Moreover, the kidney-imaging agent of the present invention is characterized in that it transiently accumulates in a kidney for a short period of time and does not remain in the kidney for a prolonged time after accumulation. In addition, the kidney-imaging agent of the present invention is characterized in that it has higher accumulation effects in an affected kidney than in a normal kidney.

EMBODIMENTS FOR CARRYING OUT THE INVENTION

Figure 1:
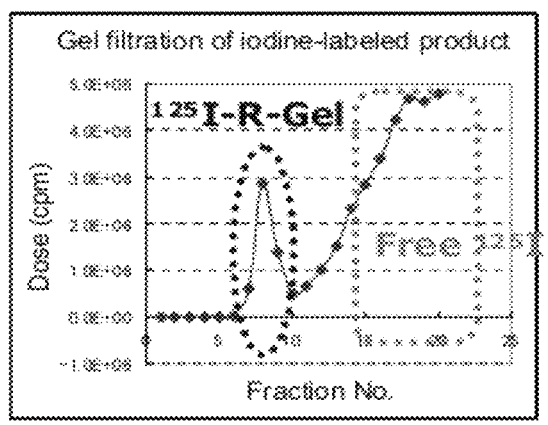
FIG. 1 shows $^{125}I$-labeling of R-Gel.

Embodiments for carrying out the present invention are described in detail below.

The type of the gelatin-like protein used in the present invention is not particularly limited, as long as it exhibits the effects of the present invention. The gelatin-like protein of the present invention is preferably any one of gelatin, collagen, fibronectin, pronectin and vitronectin, or a combination thereof. The origin of the gelatin-like protein is not particularly limited. The gelatin-like protein is preferably gelatin, and particularly preferably a recombinant gelatin.

As a recombinant gelatin that can be used in the present invention, a recombinant gelatin having an amino acid sequence derived from a partial amino acid sequence of collagen can be used. Examples of a recombinant gelatin that can be used include, but are not limited to, recombinant gelatins described in EP1014176A2, U.S. Pat. No. 6,992,172, WO2004-85473, and WO2008/103041. A recombinant gelatin preferably used as the recombinant gelatin of the present invention is described below.

The recombinant gelatin used in the present invention has original properties of naturally occurring gelatin and thus it is highly biocompatible. In addition, the recombinant gelatin is not directly obtained from natural sources and thus has no risk of causing BSE or the like. In this regard, it has an excellent property of being non-infectious. In addition, the recombinant gelatin used in the present invention is more homogenous than naturally occurring gelatin. Further, the recombinant gelatin has a predetermined sequence. Thus, it is possible to precisely design the recombinant gelatin in terms of strength and degradability with few errors by crosslinking or the like described below.

The molecular weight of the recombinant gelatin used in the present invention is preferably 2 KDa to 100 KDa, more preferably 2.5 KDa to 95 KDa, further preferably 5 KDa to 90 KDa, and most preferably 10 KDa to 90 KDa.

Preferably, the recombinant gelatin used in the present invention contains repeats of a sequence represented by Gly-X-Y characteristic to collagen. Here, a plurality of sequences each represented by Gly-X-Y may be the same or different. Gly in Gly-X-Y represents glycine. X and Y in Gly-X-Y represent any amino acids (and preferably any amino acids other than glycine). When gelatin/collagen is compared with other proteins in terms of the amino acid composition or sequence, the GXY sequence is characteristic to collagen and forms a highly specific partial structure. Glycine accounts for approximately one-third of the partial structure as a whole. Glycine is repeatedly found in the amino acid sequence at a rate of 1 out of every 3 amino acids. Glycine is the simplest amino acid. There are few restrictions to arrangement of the molecular chain of glycine and thus glycine highly contributes to regeneration of the helix structure upon gelatinization. Preferably, an amino acid represented by X or Y is rich in imino acid (proline or oxyproline) and the imino acid accounts for 10% to 45% of the amino acid sequence as a whole. Amino acids forming the GXY repeat structure account for preferably 80% or more, more preferably 95% or more, and most preferably 99% or more of the amino acid sequence as a whole.

A generally available gelatin contains charged polar amino acids and uncharged polar amino acids at a ratio of 1:1. Here, the term "polar amino acid" specifically refers to cysteine, aspartic acid, glutamic acid, histidine, lysine, asparagine, glutamine, serine, threonine, tyrosine, or arginine. In particular, the term "uncharged polar amino acid" refers to cysteine, asparagine, glutamine, serine, threonine, or tyrosine. The percentage of polar amino acids relative to all amino acids constituting the recombinant gelatin used in the present invention is 10% to 40% and preferably 20% to 30%. In addition, the percentage of uncharged polar amino acids relative to the polar amino acids is preferably 5% to less than 20% and more preferably less than 10%. Further, the amino acid sequence does not contain one amino acid and preferably two amino acids or more selected from among serine, threonine, asparagine, tyrosine, and cysteine.

In general, it is known that a polypeptide contains a minimal amino acid sequence that functions as a cell adhesion signal sequence (e.g., "Pathophysiology" (*Byotai Seiri*) Vol. 9, No. 7 (1990), p. 527, Nagai Shoten Co., Ltd.). It is preferable for a single molecule of the recombinant gelatin used in the present invention to have at least two cell adhesion signal sequences. Specifically, amino acids are shown by one-letter notation in a cell adhesion signal sequence. In view of an increase in types of adhering cells, examples of such sequence are: preferably an RGD sequence, an LDV sequence, an REDV (SEQ ID NO: 3) sequence, a YIGSR (SEQ ID NO: 4) sequence, a PDSGR (SEQ ID NO: 5) sequence, an RYVVLPR (SEQ ID NO: 6) sequence, an LGTIPG (SEQ ID NO: 7) sequence, an RNIAEIIKDI (SEQ ID NO: 8) sequence, an IKVAV (SEQ ID NO: 9) sequence, an LRE sequence, a DGEA (SEQ ID NO: 10) sequence, and an HAV sequence, more preferably an RGD sequence, a YIGSR (SEQ ID NO: 4) sequence, a PDSGR (SEQ ID NO: 5) sequence, an LGTIPG (SEQ ID NO: 7) sequence, an IKVAV (SEQ ID NO: 9) sequence, and an HAV sequence; and particularly preferably an RGD sequence. Among the RGD sequence, an ERGD (SEQ ID NO: 11) sequence is preferred.

In terms of arrangement of RGD sequences in the recombinant gelatin used in the present invention, the number of amino acids present between two RGD sequences is preferably 0 to 100 and more preferably 25 to 60. Preferably, the number of amino acids is not uniformly determined.

In view of cell adhesion/growth, the number of such minimal amino acid sequences in a single protein molecule is preferably 3 to 50, more preferably 4 to 30, particularly preferably 5 to 20, and most preferably 12.

The percentage of RGD motifs in the recombinant gelatin used in the present invention related to the total number of amino acids is preferably at least 0.4%. If the recombinant gelatin comprises 350 amino acids or more, each stretch of 350 amino acids contains preferably at least one RGD motif. The percentage of RGD motifs related to the total number of amino acids is more preferably at least 0.6%, further preferably at least 0.8%, still further preferably at least 1.0%, even further preferably at least 1.2%, and most preferably at least 1.5%. The number of ROD motifs in the recombinant gelatin is preferably at least 4, more preferably 6, further preferably 8, and even further preferably 12 to 16 per 250 amino acids. A percentage of ROD motifs of 0.4% corresponds to at least one RGD sequence per 250 amino acids. The number of ROD motifs is represented by an integer. Therefore, in order to achieve a percentage of RGD motifs of 0.4%, it is necessary for a gelatin comprising 251 amino acids to contain at least two ROD sequences. Preferably, the recombinant gelatin of the present invention contains at least 2 RGD sequences per 250 amino acids, more preferably at least 3 RGD sequences per 250 amino acids, and further preferably at least 4 RGD sequences per 250 amino acids. In another embodiment, the recombinant gelatin of the present invention comprises at least 4, preferably 6, more preferably 8, and further preferably 12 to 16 RGD motifs.

In addition, the recombinant gelatin may be partially hydrolyzed.

Preferably, the recombinant gelatin used the present invention has a structure comprising repeats of A-[(Gly-X-Y)n]m-B. Here, "m" is an integer of preferably 2 to 10 and more preferably 3 to 5. In addition, "n" is an integer of preferably 3 to 100, more preferably 15 to 70, and most preferably 50 to 65.

Preferably, a plurality of naturally occurring collagen sequence units are bound to form a repeat unit. The term "naturally occurring collagen" used herein may refer to any naturally occurring collagen. However, preferable examples thereof include type-I, type-II, type-III, type-IV, and type-V collagens. More preferably, type-I, type-II, and type-III collagens are used. In another embodiment, the origin of such collagen is preferably a human, bovine, pig, mouse, or rat and it is more preferably a human.

The isoelectric point of the recombinant gelatin used in the present invention is preferably 5 to 10, more preferably 6 to 10, and further preferably 7 to 9.5.

Preferably, the recombinant gelatin is not deaminated.

Preferably, the recombinant gelatin is not procollagen or does not comprise procollagen.

Preferably, the recombinant gelatin does not comprise telopeptide.

Preferably, the recombinant gelatin is a substantially pure collagen material prepared from a nucleic acid encoding a naturally occurring collagen.

Particularly preferably, the recombinant gelatin used in the present invention is a recombinant gelatin having the following (1) or (2):

(1) the amino acid sequence shown in SEQ ID NO: 1; or (2) an amino acid sequence having 80% or more, more preferably 90% or more, and most preferably 95% or more homology to the amino acid sequence shown in SEQ ID NO: 1, and having an action to accumulate in kidney.

The recombinant gelatin used in the present invention can be produced by a gene recombination technique known to persons skilled in the art. For instance, it can be produced according to the method described in EP1014176A2, U.S. Pat. No. 6,992,172, WO2004/85473, or WO2008/103041. Specifically, a transformant is produced by obtaining a gene encoding the amino acid sequence of a predetermined recombinant gelatin, incorporating the gene into an expression vector to prepare a recombinant expression vector, and introducing the vector into an appropriate host. The obtained transformant is cultured in an appropriate medium to produce a recombinant gelatin. Therefore, the recombinant gelatin used in the present invention can be prepared by collecting the produced recombinant gelatin from the culture product.

If the obtained recombinant gelatin alone has insufficient properties, it may be mixed with other material, or a complex of recombinant gelatin and other material may be prepared. For example, it can be mixed with a different type of recombinant gelatin or a different biopolymer or synthetic polymer. Examples of a biopolymer include a polysaccharide, a polypeptide, a protein, a nucleic acid, and an antibody. Preferably, a polysaccharide, a polypeptide, or a protein is used. Examples of a polysaccharide, a polypeptide and a protein include collagen, gelatin, albumin, fibroin, and casein. Further, the above biopolymers may be partially chemically modified according to need. For instance, hyaluronic acid ethyl ester can be used. Examples of a polysaccharide include glycosaminoglycan represented by hyaluronic acid or heparin, chitin, and chitosan. Further, examples of a polyamino acid include poly-γ-glutamic acid.

The recombinant gelatin of the present invention can be chemically modified depending on the application thereof. Chemical modification may be performed via introduction of a low molecular compound or a different polymer (e.g., a biopolymer (sugar or protein), a synthetic polymer, or polyamide) into a carboxyl group or an amino group of a side chain of the recombinant gelatin or crosslinking between recombinant gelatin chains. For example, a carbodiimide-based condensing agent is used for introduction of a low molecular compound into the recombinant gelatin.

The crosslinking agent used in the present invention is not particularly limited, as long as the present invention can be carried out. It may be a chemical crosslinking agent or an enzyme. Examples of a chemical crosslinking agent include formaldehyde, glutaraldehyde, carbodiimide, and cyanamide. Preferably, formaldehyde or glutaraldehyde is used. Further, crosslinking of a recombinant gelatin can be conducted by light irradiation to a gelatin into which a photoreactive group has been introduced, light irradiation under the presence of a photosensitizer, or the like. Examples of a photoreactive group include a cinnamyl group, a coumarin group, a dithiocarbamyl group, xanthene dye, and camphorquinone.

In a case in which enzymatic crosslinking is carried out, an enzyme used is not particularly limited, as long as it has an action of causing crosslinking between recombinant gelatin chains. However, crosslinking can be carried out using preferably transglutaminase or laccase and most preferably transglutaminase. Examples of proteins that are enzymatically crosslinked by transglutaminase include, but are not particularly limited to, proteins having lysine residues and glutamine residues. A mammalian-derived or microorganism-derived transglutaminase may be used. Specific examples thereof include: the Activa series (produced by Ajinomoto Co., Inc.); commercially available mammalian-derived transglutaminases serving as reagents such as guinea pig liver-derived transglutaminase, goat-derived transglutaminase, and rabbit-derived transglutaminase (produced by Oriental Yeast Co., Ltd., Upstate USA Inc., Biodesign International, etc.); and a human-derived blood coagulation factor (Factor XIIIa, Haematologic Technologies, Inc.).

Crosslinking of the recombinant gelatin comprises the following two steps: a step of mixing a recombinant gelatin solution and a crosslinking agent; and a step of causing a reaction in the obtained homogenous solution.

According to the present invention, the mixing temperature for treating the recombinant gelatin with a crosslinking agent is not particularly limited, as long as the solution can be homogenously agitated. However, it is preferably 0° C. to 40° C., more preferably 0° C. to 30° C., further preferably 3° C. to 25° C., still further preferably 3° C. to 15° C., even further preferably 3° C. to 10° C., and particularly preferably 3° C. to 7° C.

After agitation of the recombinant gelatin and the crosslinking agent, the temperature can be increased. The reaction temperature is not particularly limited, as long as crosslinking can proceed. However, in view of denaturation or degradation of the recombinant gelatin, it is substantially 0° C. to 60° C., preferably 0° C. to 40° C., more preferably 3° C. to 25° C., further preferably 3° C. to 15° C., still further preferably 3° C. to 10° C., and particularly preferably 3° C. to 7° C.

According to the present invention, the above-described gelatin-like protein (particularly preferably, a recombinant gelatin having an amino acid sequence derived from a partial amino acid sequence of collagen) is administered to a subject (e.g. a mammal such as a human), so that a labeled probe can be targeted to a kidney. That is to say, according to the present invention, since a gelatin-like protein targets to a kidney and accumulates therein, a desired labeled probe can be delivered to the kidney as a target. Accordingly, in the present invention, the gelatin-like protein can be used as a kidney-imaging agent.

The kidney-imaging agent of the present invention can comprises a labeled probe together with the gelatin-like protein. Examples of a labeled probe include a fluorescent dye, a radioisotope, a nuclide used for PET, a nuclide used for SPECT, an MRI contrast medium, a CT contrast medium, and a magnetic material. Preferred examples of the radioisotope, the nuclide used for PET, and the nuclide used for SPECT (single photon emission computed tomography) include $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{186/188}$Re, $^{125}$I, a complex thereof, and a combination thereof. Examples of the MRI contrast medium, the CT contrast medium, and the magnetic material include gadolinium, Gd-DTPA, Gd-DTPA-BMA, Gd-HP-DO3A, iodine, iron, iron oxide, chromium, manganese, and a complex or chelate complex thereof. Moreover, examples of the fluorescent dye include a known quantum dot, indocyanine green, and a near-infrared fluorescent dye (Cy5.5, Cy7, AlexaFluoro, etc.).

Preferably, the gelatin-like protein is physically or chemically bound to the labeled probe directly or via a linker. Specifically, the bond is preferably a coordinate bond, a covalent bond, a hydrogen bond, hydrophobic interaction, or physical adsorption. In all cases, a bond, a linker and a binding method, which have been known, can be adopted.

The kidney-imaging agent of the present invention is characterized in that it widely accumulates in an affected kidney and shows different levels of accumulation in a normal kidney and an affected kidney. Examples of kidney diseases include, but are not limited to, glomerulonephritis, IgA nephropathy, diabetic nephropathy, membranous nephropathy, hydronephrosis, contrast nephropathy, pyelonephritis, renal failure, acute nephritis, chronic nephritis, interstitial nephritis, renal disorder, nephrotic syndrome, hypertensive nephrosclerosis, diabetic glomerulosclerosis, nephrolithiasis, amyloid nephropathy, renal vein thrombosis, Alport syndrome, and kidney tumor.

The dose, the usage, and the dosage form of the kidney-imaging agent of the present invention can be appropriately determined depending of the purpose of use. For example, the kidney-imaging agent of the present invention can be directly administered in vivo to a desired site. Alternatively, it may be suspended in a liquid excipient such as an aqueous solvent (e.g., distilled water for injection, physiological saline for injection, or buffer (e.g., phosphate or citrate buffer) (pH 5 to 8)) so as to be administered via injection, external application, or the like. In addition, it may be mixed with an adequate excipient in the form of ointment, gel, cream, or the like so as to be externally applied. That is, the administration route of the kidney-imaging agent of the present invention may be the oral route or the parenteral route (e.g., intravenous administration, intramuscular administration, subcutaneous administration, or intradermal administration). Examples of the dosage form include: oral administration agents such as tablets, powders, capsules, granules, extracts, and syrups; and parenteral administration agents such as injections (e.g., intravenous injections, muscular injections, subcutaneous injections, and intradermal injections).

A formulation of the kidney-imaging agent of the present invention can be prepared by a method known to persons skilled in the art. For example, if liquid is used as a carrier for a formulation, the kidney-imaging agent of the present invention can be dissolved or dispersed in the liquid. Alternatively, if a powder is used as a carrier for a formulation, the kidney-imaging agent of the present invention can be mixed with or adhere to the powder. Further, if necessary, a pharmaceutically acceptable additive (e.g., a preservative, a stabilizer, an antioxidant, an excipient, a binder, a disintegrator, a wetting agent, a lubricant, a coloring agent, an aromatic agent, a corrigent, a coating, a suspending agent, an emulsifier, a dissolution adjuvant, a buffer, a tonicity agent, a plasticizer, a surfactant, or a soothing agent) can be mixed therewith.

The applied dose of the recombinant gelatin is not particularly limited. However, for example, it can be 10 μg/kg to 100 mg/kg, and preferably 100 μg/kg to 10 mg/kg per kg of body weight of a subject organism, to which it is to be administered.

The present invention is hereafter described in greater detail with reference to the following examples, although the present invention is not limited thereto.

EXAMPLES

As a recombinant gelatin, CBE3 (WO2008-103041) described below was prepared.

CBE3

Molecular weight: 51.6 kD

Structure: GAP[(GXY)63]3G

Number of amino acids: 571

Number of RGD sequences: 12

Imino acid content: 33%

(Substantially 100% of amino acids form the GXY repeat structure. The amino acid sequence of CBE3 does not contain any of serine, threonine, asparagine, tyrosine, and cysteine. CBE3 has the ERGD (SEQ ID NO: 11) sequence).

Isoelectric point: 9.34

Amino acid sequence (SEQ ID NO: 1 in the Sequence Listing) (This amino acid sequence corresponds to the amino acid sequence shown in SEQ ID NO: 3 in WO2008/103041. Note that "X" at the end was modified to "P.")

GAP (GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP) 3G

In the Examples described below, the above recombinant gelatin described as "CBE3" is referred to as "R-Gel" unless otherwise specified.

In addition, as is understood based on its composition, R-Gel is a polypeptide/protein consisting of amino acids, which is a bioabsorbable material.

(1) Iodide ($^{125}$I) Labeling of R-Gel

R-Gel was labeled with $^{125}$I by a chloramine T method.

R-Gel (1 mg) was dissolved in buffer A (0.5 M phosphate buffer, 0.5 M NaCl, pH 7.5) (1 mL). A NaI/NaOH solution (5 μL) was added to 200 μL of the obtained solution. A 0.2 mg/mL chloramine T/buffer A solution (100 μL) (chloramine T: Nacalai Tesque) was further added thereto, followed by vortex mixing for 2 minutes. Then, a 4 mg/mL SMS (sodium metabisulfite) aqueous solution (100 μL) was added thereto, followed by vortex mixing for 2 minutes (liquid mixture B).

The liquid mixture B was applied to a PD-10 column (GE Healthcare) that had been equilibrated in advance with PBS (phosphate buffer), followed by elution with PBS. The eluate was fractionated (500 μL, for each fraction) and the fractions were collected. The γ-ray radiation dose for each collected fraction was determined using an auto well gamma system (ARC-380: Aloka) to determine the $^{125}$I level in each fraction. $^{125}$I-labeled R-Gel and free $^{125}$I were separated (FIG. 1).

Accordingly, $^{125}$I-labeled R-Gel was obtained (hereinafter referred to as "$^{125}$I-R-Gel"). In addition, a BCA method (BCA Protein Assay Reagent: Pierce) was used for protein quantification. 0.1 mg/mL and 15,000,000 cpm/mL $^{125}$I-R-Gel/PBS solutions were obtained.

In addition, for comparative examination, beef-bone-derived alkali-treated gelatin (hereinafter referred to as animal gelatin) having a weight concentration equivalent to that of R-Gel was processed in the above manner. Thus, $^{125}$I-animal gelatin was prepared.

(2) Administration of $^{125}$I-R-Gel to a DDY Mouse

The $^{125}$I-R-Gel prepared above (200 μL) was administered via the caudal vein to a DDY mouse (a 6-week-old male mouse: Japan SLC). The tissue distribution of $^{125}$I-R-Gel was obtained by determining the γ-ray radiation dose in each organ/tissue and the γ-ray radiation dose in excreted urine using an auto well gamma system (ARC-380: Aloka) immediately and 1, 3, 6, and 24 hours after administration. The γ-ray radiation dose in an organ/tissue was directly measured by dissecting the mouse. In addition, the blood γ-ray radiation dose was determined by calculating the γ-ray radiation dose in 200 μL of blood obtained by heart blood sampling.

The γ-ray radiation dose with respect to the amount of administered $^{125}$I-R-Gel was obtained by subtracting "the γ-ray radiation dose in $^{125}$I-R-Gel remaining in a syringe after administration via the caudal vein" from "the γ-ray radiation dose in $^{125}$I-R-Gel filling a syringe." In addition, the total blood volume was designated as accounting for 8% of the body weight for calculation. $^{125}$I-R-Gel accumulated in a thyroid gland accounted for 1% or less of the total amount of administered $^{125}$I-R-Gel. It was found that there was substantially no free $^{125}$I and $^{125}$I remained bound to R-Gel.

The "amount of $^{125}$I-R-Gel remaining in vivo" was obtained by adding the γ-ray radiation doses in all organs/tissues except for the γ-ray radiation dose in excreted urine.

The "percentage of $^{125}$I-R-Gel remaining in vivo" was obtained by dividing the "amount of $^{125}$I-R-Gel remaining in vivo" by the γ-ray radiation dose upon administration of $^{125}$I-R-Gel.

Figure 2:
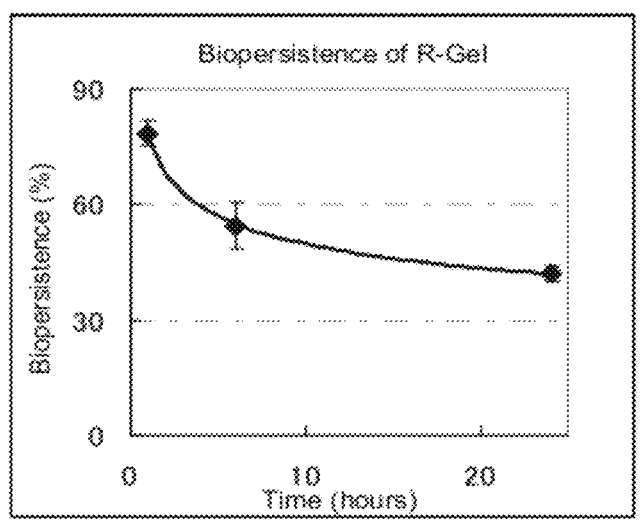
FIG. 2 shows R-Gel biopersistence (the percentage of R-Gel remaining in vivo).

Accordingly, it was found that 40% or more of $^{125}$I-R-Gel remains in vivo even 24 hours after administration (FIG. 2). It is known that the percentage of a low molecular compound remaining in vivo is very low as a result of urine excretion. For example, PM Van Hagen et al demonstrated that 85% or more of a low-molecular cyclic RGD peptide (cyclic-RGDyK) is excreted in urine 24 hours after administration, that is to say, the amount of the peptide remaining in vivo is 15% or less (Evaluation of a radiolabelled cyclic DTPA-RGD analogue for tumor imaging and radionuclide therapy. Int. Journal of Cancer 2000; 90: 186-198). It is understood that R-Gel itself has good biopercsistence.

Figure 3:
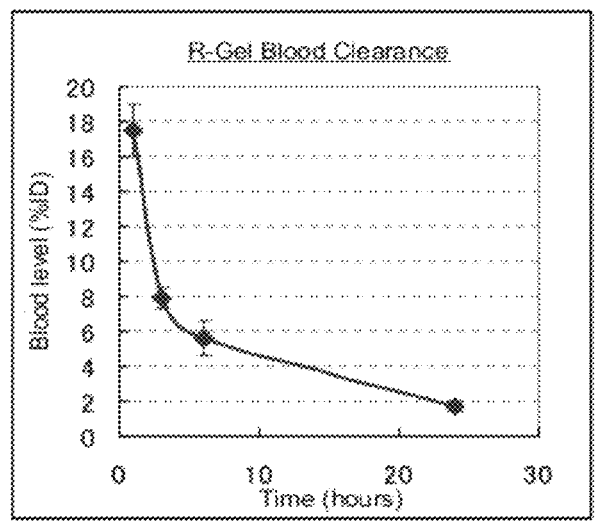
FIG. 3 shows R-Gel blood clearance.

In addition, when $^{125}$I-R-Gel blood clearance was determined based on the blood level expressed by % ID (% of Injected Dose), the blood level (% ID) at a certain time after administration was 17.5±1.5% in 1 hour, 7.9±0.6% in 3 hours, 5.6±1.0% in 6 hours, and 1.7±0.3% in 24 hours (shown as the average±S.D.) (FIG. 3). RGD peptides, which are low-molecular substances, cyclic RGD peptides, and analogs thereof were quickly excreted from the body, showing rapid blood clearance. Therefore, it is understood that R-Gel shows persistence in blood at high levels. Regarding blood clearance, for example, the blood level of $^{64}$Cu-DOTA-E{E[cyclic-(RGDfK)]$_2$}$_2$ which is a tetrameric peptide constituent of cyclic RGD (cylclic-RGDfK), is 0.61±0.01% in 30 minutes and 0.21±0.01% in 4 hours after administration, indicating very quick blood clearance. This was demonstrated by Wu Y, Zhang X, Xiong Z, et al. (microPET imaging of glioma αVβ 3-integrin expression using 64 Cu-labeled tetrameric ROD peptide. J Nucl Med 2005; 46: 1707-18). Based on the above results, it is understood that R-Gel has "good persistence in blood" which is useful as imaging agent.

(3) Cy7-Labeling of R-Gel, Anti-Mac1 Antibody and PSK (Animal Gelatin)

R-Gel, an anti-Mac1 antibody (Rat Anti-Mouse CD11b/Mac-1, SouthernBiotech), and porcine-skin-derived gelatin (hereinafter referred to as "PSK;" Nitta Gelatin Inc.) were labeled with a fluorescent dye (Cy7).

As Cy7, Cy7 mono-reactive NHS ester (GE Healthcare) was used herein. Cy7 NHS ester was dissolved in DMSO (dimethylsulfoxide) to result in a concentration of 10 mg/mL. Cy7 NHS ester/DMSO (10 µL) and R-Gel (1 mg) were mixed in 0.1 M sodium carbonate buffer (pH 9.3). The mixture was reacted under light shielded conditions at room temperature for 1 hour. The obtained reaction product was applied to a PD-10 column (GE Healthcare) that had been equilibrated with PBS (phosphate buffer) in advance, followed by elution with a sufficient amount of PBS. The amount of fluorescence in the eluate was determined so as to separate Cy7-labeled R-Gel (hereinafter referred to as "Cy7-R-Gel") and an unreacted product of Cy7. Thus, Cy7-R-Gel was obtained.

Similarly, Cy7 NHS ester/DMSO (10 µL) and an anti-Mac1 antibody (1 mg) were mixed in 0.1 M sodium carbonate buffer (pH 9.3). The mixture was reacted under light shielded conditions at room temperature for 1 hour. The obtained reaction product was applied to a PD-10 column that had been equilibrated with PBS (phosphate buffer) in advance, followed by elution with a sufficient amount of PBS. The amount of fluorescence in the eluate was determined so as to separate a Cy7-labeled anti-Mac1 antibody (hereinafter referred to as "Cy7-anti-Mac1 antibody") and an unreacted product of Cy7. Thus, a Cy7-anti-Mac1 antibody was obtained.

Similarly, Cy7 NHS ester/DMSO (10 µL) and PSK (1 mg) were mixed in 0.1 M sodium carbonate buffer (pH 9.3). The mixture was reacted under light shielded conditions at room temperature for 1 hour. The obtained reaction product was applied to a PD-10 column that had been equilibrated with PBS (phosphate buffer) in advance, followed by elution with a sufficient amount of PBS. The amount of fluorescence in the eluate was determined so as to separate Cy7-labeled PSK (hereinafter referred to as "Cy7-PSK") and an unreacted product of Cy7. Thus, Cy7-PSK was obtained.

(4) Preparation of Unilateral Ureteral Obstructed (UUO) Model Animals

Unilateral ureteral obstructed models (hereinafter referred to as "UUO models") were produced as acute nephritis, interstitial nephritis, interstitial renal disorder and renal failure model animals. Mice (6-week-old male C57BL6 and DDY mice) (CLEA Japan, Japan SLC) were used as subject animals. UUO treatment was performed under nembutal anesthesia in the following manner. A urinary duct located immediately below the left kidney was ligated at two sites with nylon suture. The urinary duct was cut between the two ligated sites. The abdominal incision was sutured. Each mouse was disinfected and raised. As a result, the left kidney was designated as a UUO kidney, and the right kidney was designated as a normal kidney for each mouse.

(5) Observation of Pathological Conditions of UUO Models

Figure 4:
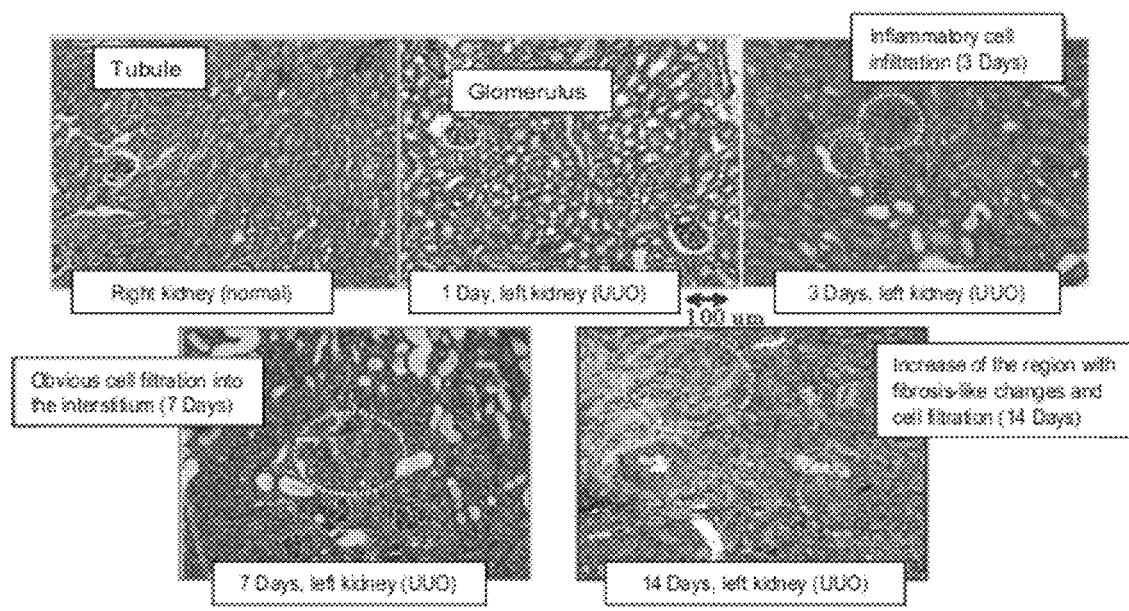
FIG. 4 shows changes in pathological conditions of the kidney of a UUO model (HE-stained tissue sections).
Figure 5:
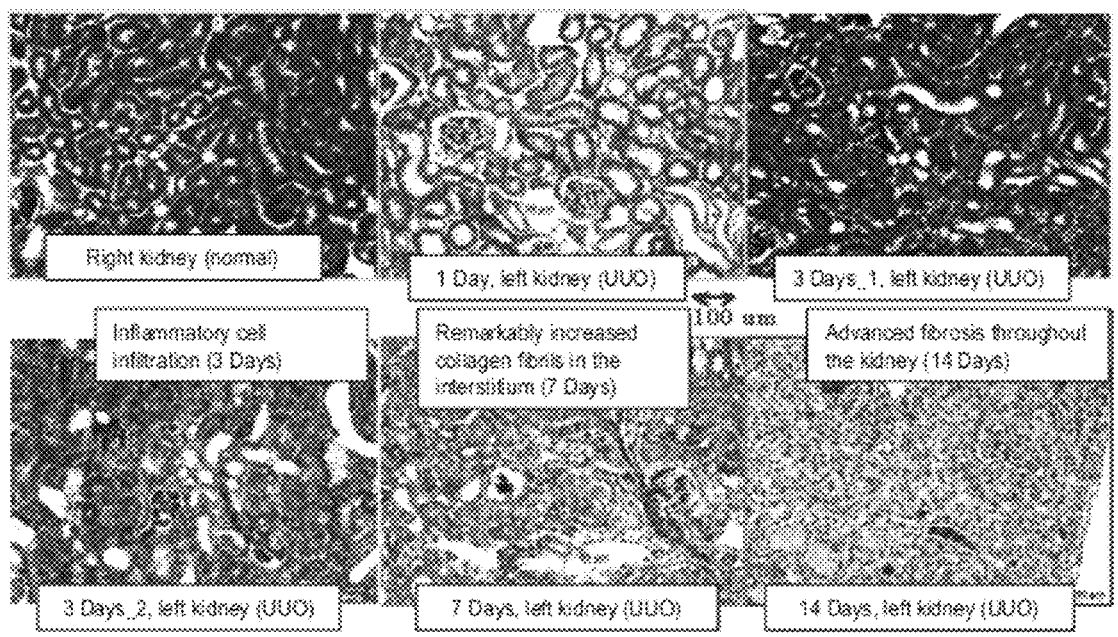
FIG. 5 shows changes in pathological conditions of the kidney of a UUO model (MT-stained tissue sections).

Tissue sections were prepared in a time-dependent manner after UUO from left kidneys and normal right kidneys. Each kidney was excised with physiological saline perfusion. The excised kidney tissues were fixed with 10% formalin and paraffin-embedded. Thus, tissue sections were prepared. For staining, HE (hematoxylin-eosin) staining and MT (Masson trichrome) staining were performed. FIGS. 4 and 5 show tissue sections after staining. The results show that UUO treatment caused nephritis of the left kidney. In addition, inflammatory cell filtration was obviously observed since 3 days after the treatment.

(6) R-Gel Accumulation in the Affected Kidney of UUO Model

The Cy7-anti-Mac1 antibody (200 µL) prepared in (3) was administered via the caudal vein to a UUO model on Day 3 after UUO treatment. The anti-Mac1 antibody is an antibody against Mac1 expressed on cell surfaces. It is known that Mac1 is expressed on inflammatory cell macrophage surfaces. The mouse was photographed 24 hours after administration of the Cy7-anti-Mac1 antibody, followed by fluorescence signal detection and determination/imaging, using an LAS5000 luminescent image analyzer (trial model; FUJIFILM Corporation). A visible light image and a fluorescent image were simultaneously photographed and superimposed so as to identify a fluorescence emitting region. For fluorescent image photographing, an epifluorescent IR light source was used as a light source and a 785-nm bandpass filter was used as a filter. The MultiGauge software (FUJIFILM Corporation) was used for image analysis/signal intensity quantification. The light source and the filter used herein are appropriate for Cy7 fluorescence signal detection.

Figure 6:
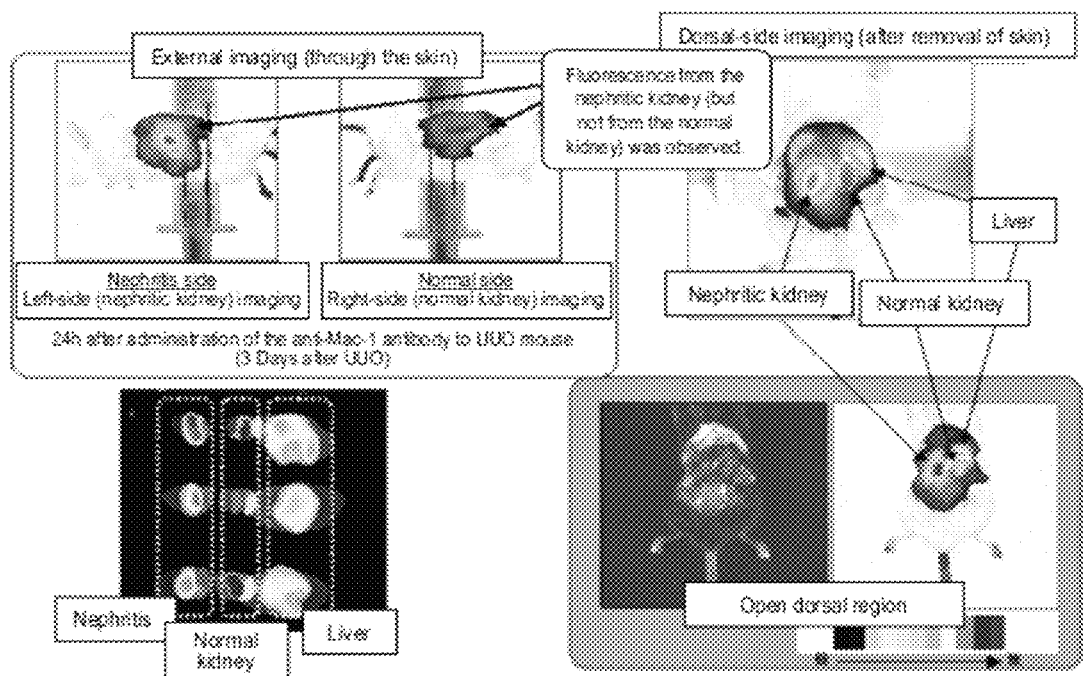
FIG. 6 shows accumulation of the anti-Mac1 antibody in the nephritic kidney of a UUO model.

As a result, imaging of a left kidney (affected kidney) treated with a Cy7-anti-Mac1 antibody was successfully carried out. At such time, the detection signals from the left kidney serving as an affected kidney were significantly higher than the fluorescence signals detected from the right kidney serving as a normal kidney (FIGS. 6 and 8).

Similarly, Cy7-R-Gel (200 µL) prepared in (3) above was administered via the caudal vein to a UUO model on Day 3 after UUO treatment. The mouse was photographed 24 hours after administration of Cy7-R-Gel, followed by fluorescence signal detection and determination/imaging, using an LAS5000 luminescent image analyzer (trial model; FUJIFILM Corporation). A visible light image and a fluorescent image were simultaneously photographed and superimposed so as to identify a fluorescence emitting region. For fluorescent image photographing, an epifluorescent IR light source was used as a light source and a 785-nm bandpass filter was used as a filter. The MultiGauge software (FUJIFILM Corporation) was used for image analysis/signal intensity quantification. The light source and the filter used herein are appropriate for Cy7 fluorescence signal detection.

Figure 7:
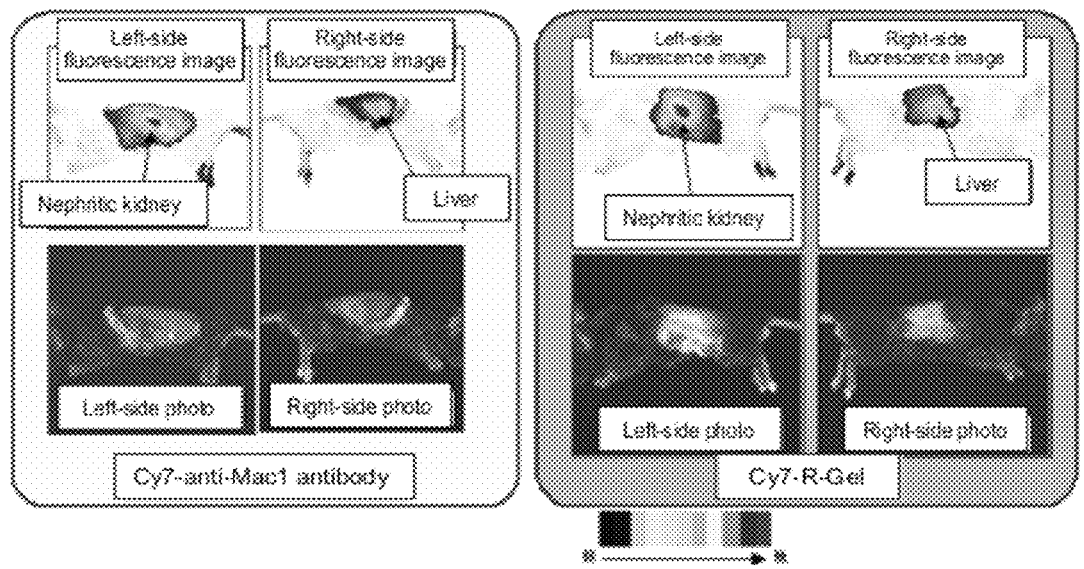
FIG. 7 shows accumulation of the anti-Mac1 antibody and R-Gel in the nephritic kidney.

As a result, imaging of a left kidney (affected kidney) treated with Cy7-R-Gel was successfully carried out. At such time, the detection signals from the left kidney serving as an affected kidney were significantly higher than the fluorescence signals detected from the right kidney serving as a normal kidney (FIGS. 7 and 8). The results revealed that R-Gel accumulates in an affected kidney to a significantly greater extent than in a normal kidney.

Figure 8:
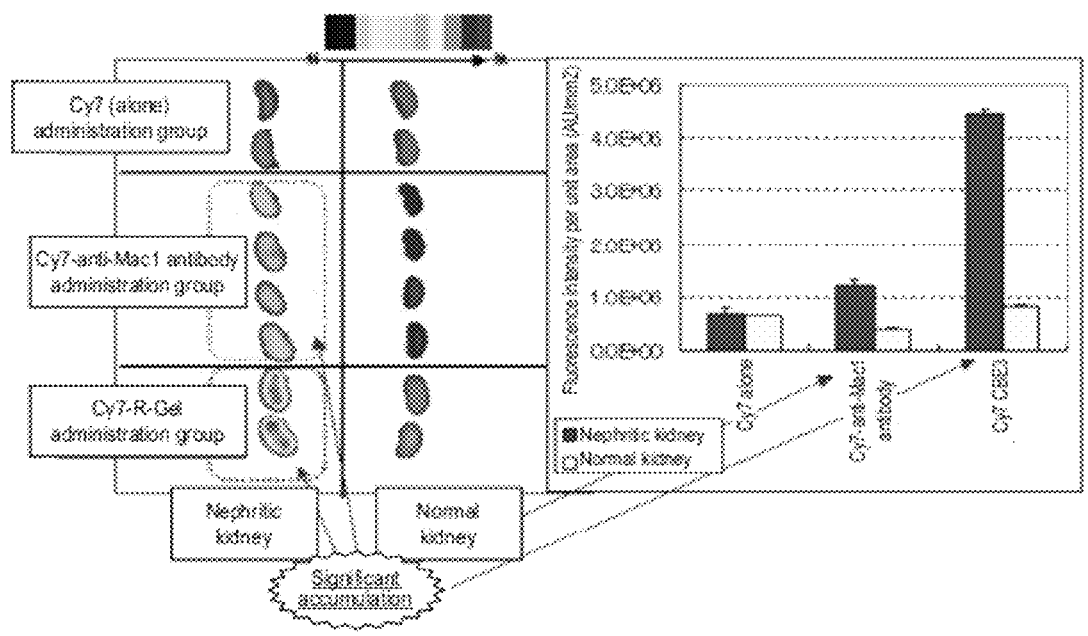
FIG. 8 shows accumulation of R-Gel and the anti-Mac1 antibody in the nephritic kidney of a UUO model.

In addition, FIG. 8 shows images of the right kidney and the left kidney photographed by LAS5000 under identical conditions, each kidney having been excised by cutting the urinary duct immediately below the kidney with perfusion with a sufficient amount of physiological saline. It is shown that there was no significant difference in accumulation of the Cy7 dye between the left kidney and the right kidney in a group to which the Cy7 dye alone had been administered via the caudal vein, while on the other hand, the anti-Mac1 antibody and R-Gel accumulated in the left kidney to a significantly greater extent than in the right kidney in the group to which the anti-Mac1 antibody and R-Gel had been administered.

Therefore, the affected kidney-targeting agent provided with R-Gel of the present invention has high ability to accumulate in a kidney affected with acute nephritis, interstitial nephritis, interstitial renal disorder, or renal failure to a greater extent than in a normal kidney.

(7) Preparation of a Mouse Model with Spontaneous IgA Nephropathy (HIGA Mouse)

HIGA mice (Japan SLC) were used as model animals with IgA nephropathy and glomerulonephritis. In addition, it is known that HIGA mice usually take about 25 weeks until the spontaneously onset of a disease. However, in this Example, the spontaneous onset was promoted by unilateral nephrectomy. Eight-week-old female HIGA mice were subjected to unilateral nephrectomy and raised for another 8 weeks (until they became 16 weeks old). Unilateral nephrectomy was performed by a general nephrectomy technique. Specifically, nephrectomy was performed after ligation of the renal artery and the renal vein.

(8) Observation of Pathological Conditions of HIGA Mice

Figure 9:
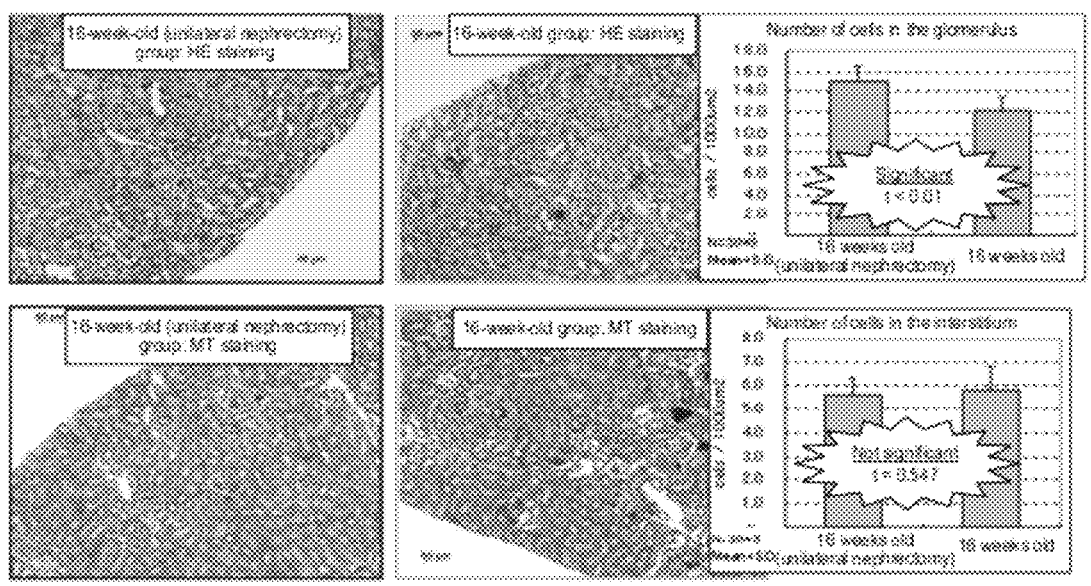
FIG. 9 shows kidney tissue sections showing the onset of glomerulonephritis in a 16-week-old HIGA mouse subjected to unilateral nephrectomy (HE staining and MT staining).

Kidney tissue sections were prepared from the above unilaterally nephrectomized 16-week-old HIGA mice for which the onset of a disease had been promoted and untreated 16-week-old HIGA mice. The tissue sections were obtained from kidney tissue subjected to perfusion with a sufficient amount of physiological saline. Formalin fixation with 10% formalin and paraffin embedding were carried out. Thus, tissue sections were prepared and subjected to HE (hematoxylin-eosin) staining and MT (Masson trichrome) staining. FIG. 9 shows each stained tissue section. Changes in inflammation/pathological conditions were digitized based on the number of tissue cells (note that the number of inflammatory cells increases due to inflammation). As a result, the number of tissue cells in the glomerulus for the unilaterally nephrectomized 16-week-old group was significantly higher than that for the untreated 16-week-old group, while on the other hand, there was no significant change in the number of cells in the interstitium between the unilaterally nephrectomized 16-week-old group and the untreated 16-week-old group. Accordingly, it was revealed that the onset of glomerulonephritis was promoted in the unilaterally nephrectomized group.

(9) Accumulation of R-Gel in the Affected Kidney of HIGA Mouse

Cy7-R-Gel (200 µL) prepared in (3) above was administered via the caudal vein to the unilaterally nephrectomized 16-week-old HIGA mice. The mouse was photographed 24 hours after administration of Cy7-R-Gel, followed by fluorescence signal detection and determination/imaging, using an LAS5000 luminescent image analyzer (trial model; FUJIFILM Corporation). A visible light image and a fluorescent image were simultaneously photographed and superimposed so as to identify a fluorescence emitting region. For fluorescent image photographing, an epifluorescent IR light source was used as a light source and a 785-nm bandpass filter was used as a filter. The MultiGauge software (FUJIFILM Corporation) was used for image analysis/signal intensity quantification. The light source and the filter used herein are appropriate for Cy7 fluorescence signal detection.

Figure 10:
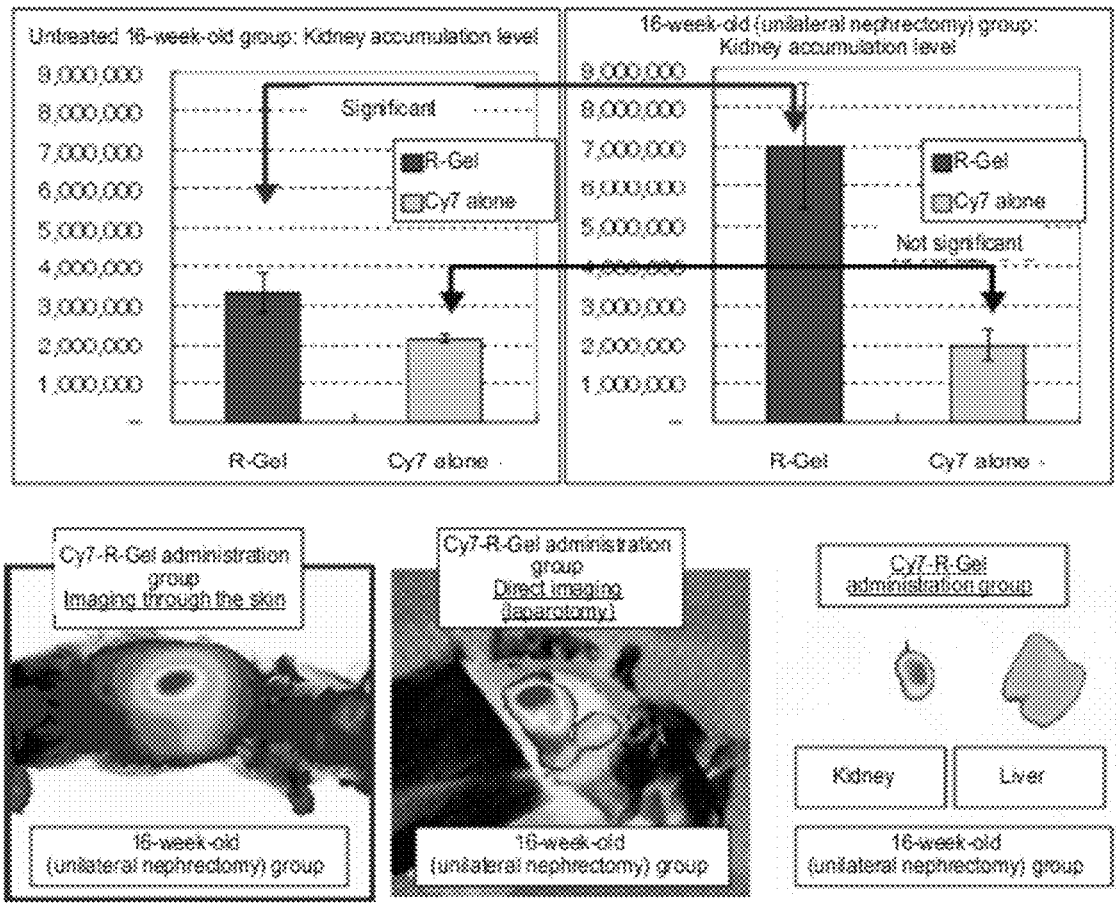
FIG. 10 shows accumulation of R-Gel in the kidney affected with IgA nephropathy.

As a result, imaging of an affected kidney of HIGA mouse treated with Cy7-R-Gel was successfully carried out. At such time, fluorescence signal levels in the affected kidney group to which Cy7-R-Gel had been administered were significantly higher than those in the group to which the equivalent amount of Cy7 alone had been administered (FIG. 10). Further, as a result of comparison of the untreated 16-week-old group, it was found that there was no significant difference between the untreated 16-week-old group to which Cy7 had been administered and the unilaterally nephrectomized 16-week-old group to which Cy7 had been administered. On the other hand, the amount of R-Gel accumulated in the kidney for the unilaterally nephrectomized 16-week-old group to which Cy7-R-Gel had been administered was significantly higher than that for the untreated 16-week-old group to which Cy7-R-Gel had been administered. Accordingly, it was revealed that R-Gel accumulates in a kidney affected with a progressive disease to a greater extent than in a relatively normal kidney. This indicates that R-Gel has a targeting ability that results in differences in terms of accumulation between a normal kidney and an affected kidney.

Accordingly, it was shown that the affected kidney-targeting agent comprising R-Gel of the present invention has high ability to accumulate in a kidney affected with nephritis, glomerulonephritis, a glomerular renal disorder, IgA nephropathy, or renal failure to a greater extent than in a normal kidney.

(10) Preparation of Ischemia-Reperfusion (I/R) Animal Model

An ischemia-reperfusion model (hereinafter referred to as "I/R model") was produced as a model animal with acute renal failure induced by ischemia reperfusion. Six-week-old male C57BL6 mice were used as model animals. The mice were subjected to ischemic treatment by clamping the renal artery and the renal vein connected to the left kidney with an artery clamp for 40 minutes to block the blood flow. This treatment causes renal disorder due to ischemia reperfusion only in the left kidney. Therefore, the right kidney can serve as a normal kidney and the left kidney can serve as an I/R-injured kidney.

It is known that the renal disorder caused by ischemia reperfusion is observed as a postoperative sequelae for a human or it takes place after reperfusion of blood after transient blocking of blood flow (which results in ischemic conditions) necessary for organ transplantation.

(11) Observation of Pathological Conditions of I/R Model Animals

Figure 11:
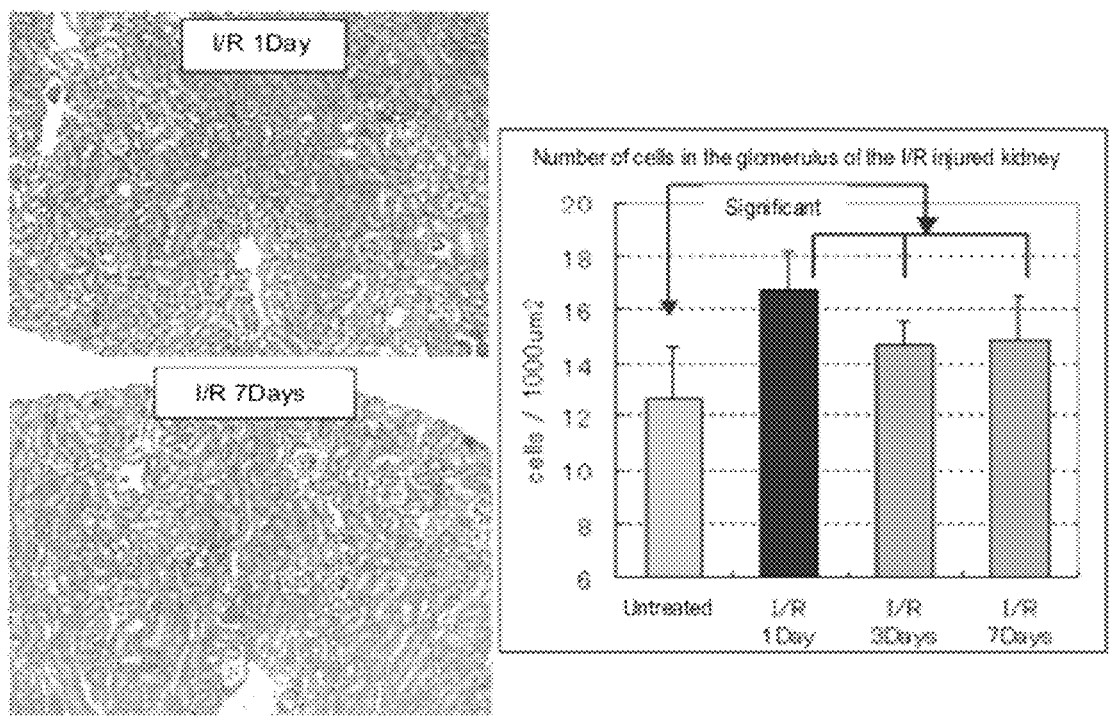
FIG. 11 shows tissue sections showing pathological conditions of renal disorder in an I/R model.

Kidney tissue sections were prepared from the above I/R mice. The tissue sections were obtained via excision from kidney tissue subjected to perfusion with a sufficient amount of physiological saline. Formalin fixation with 10% formalin and paraffin embedding were carried out. Thus, tissue sections were prepared and subjected to HE (hematoxylin-eosin) staining and MT (Masson trichrome) staining. FIG. 11 shows each stained tissue section. Changes in inflammation/pathological conditions were digitized based on the number of tissue cells (note that the number of inflammatory cells increases due to inflammation). As a result, the number of tissue cells in the glomerulus in the left kidney (I/R kidney) was found to be significantly higher than that in the right kidney (normal/untreated kidney), indicating the development of the I/R-induced renal disorder (FIG. 11). Remarkable pathological changes were observed on Day 1 after treatment. Accordingly, it was confirmed that I/R-treated ischemia-reperfusion renal disorder model was successfully produced.

(12) Accumulation of R-Gel in the Affected Kidney of an Ischemia Reperfusion (I/R) Model Animal Cy7-R-Gel (200 µL) prepared in (3) was administered via the caudal vein to an I/R model mouse. The mouse was photographed 24 hours after administration of Cy7-R-Gel, followed by fluorescence signal detection and determination/imaging, using an LAS5000 luminescent image analyzer (trial model; FUJIFILM Corporation). A visible light image and a fluorescent image were simultaneously photographed and superimposed so as to identify a fluorescence emitting region. For fluorescent image photographing, an epifluorescent IR light source was used as a light source and a 785-nm bandpass filter was used as a filter. The MultiGauge software (FUJIFILM Corporation) was used for image analysis/signal intensity quantification. The light source and the filter used herein are appropriate for Cy7 fluorescence signal detection.

Figure 12:
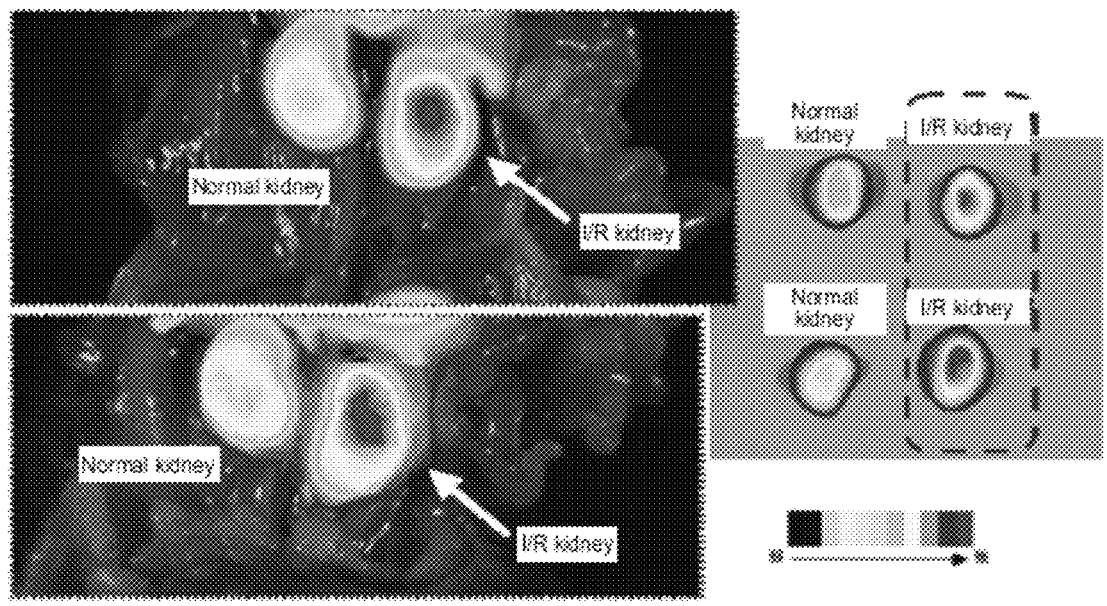
FIG. 12 shows accumulation of R-Gel in the I/R kidney.

As a result, fluorescence signals obtained from Cy7-R-Gel in the ischemia-reperfusion-injured left kidney were significantly higher than those detected from the right kidney serving as a normal kidney (FIG. 12). Accordingly, it was revealed that R-Gel accumulates in an ischemia-reperfusion-injured affected kidney to a greater extent than in a normal kidney. Specifically, it was shown that the targeting agent provided with R-Gel accumulates in a kidney affected with renal disorder to a greater extent than in a normal kidney, indicating that R-Gel has a targeting ability that causes differences in accumulation between a normal kidney and an affected kidney.

Therefore, it was shown that the affected kidney-targeting agent provided with R-Gel of the present invention has high ability to accumulate in an affected kidney with renal disorder induced by ischemia reperfusion to a greater extent than in a normal kidney.

Based on the above, it has been revealed that the affected kidney-targeting agent provided with R-Gel of the present invention has a versatile targeting ability for an affected kidney with kidney failure such as acute nephritis, interstitial nephritis, interstitial renal disorder, glomerulonephritis, glomerularrenal disorder, IgA nephropathy, or renal disorder caused by ischemia reperfusion during organ transplantation or surgery. In addition, it was shown that the agent accumulates in an affected kidney to a greater extent than in a normal kidney. Accordingly, it has become possible to provide an affected kidney-targeting agent whereby the object of the present invention can be achieved.

(13) Cell Incorporation Test Using Tubular Epithelial Cells

Next, whether or not renal tubular epithelial cells would incorporate R-Gel was experimentally confirmed by a cell incorporation test. Tubular epithelial cells were prepared. The cells used herein were human tubular epithelial cells (RPTEC: human renal proximal tubular epithelial cells; Takara Bio Inc.). A renal epithelial cell basic medium (serum-free medium) (REBM™; Takara Bio Inc.) and a renal epithelial cell medium kit (0.5% FBS) (REGM™ BulletKit™; Takara Bio Inc.) were used. $5 \times 10^6$ cells/mL RPTEC cells were added to a T-25 flask (0.125 mL per flask). Culture was carried out on a 5-mL medium (supplemented with serum and growth factors) until a sufficient amount of cells proliferated. Upon subculture and removal of cells, a 0.25% trypsin solution containing EDTA was used. Then, cells were transferred to a 35-mm cell culture dish and cultured therein. The thus obtained cells were used in the following Example.

In addition, Cy2-R-Gel was prepared by labeling R-Gel with a Cy2 dye. All of the labeling steps were aseptically conducted. Cy2 Bis-reactive NHS ester (GE Healthcare) was used as the Cy2 dye. R-Gel (5 mg) was dissolved in 0.1 M sodium carbonate buffer (700 µL, pH 9.3). Cy2 Bis reactive NHS ester (0.1 mg) was added thereto. The liquid mixture was sufficiently stirred. Then, the mixture was reacted under light shielded conditions at 37° C. for 1 hour. The obtained reaction product was applied to a PD-10 column that had been equilibrated with PBS (phosphate buffer) in advance, followed by elution with a sufficient amount of PBS. The amount of fluorescence in the eluate was determined so as to separate Cy2-labeled R-Gel (hereinafter referred to as "Cy2-R-Gel") and an unreacted product of Cy2. Thus, Cy2-R-Gel was obtained. The obtained Cy2-R-Gel was filter-sterilized before and used.

A medium (3 mL) was added to the RPTEC cells cultured in a 5-cm dish. Cy2-R-Gel (500 µL) was added thereto, followed by incubation at 37° C. for 3 hours. Then, the cells were washed with a sufficient amount of PBS buffer for the sufficient number of times.

Figure 13:
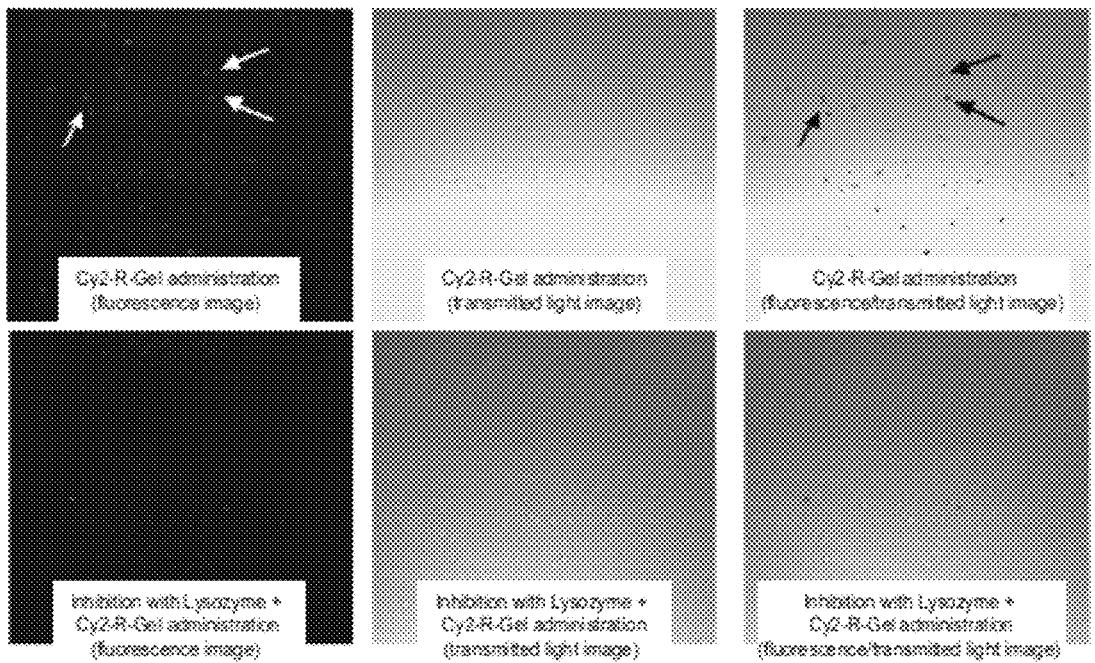
FIG. 13 shows incorporation of R-Gel by tubular epithelial cells (confocal laser microscopic image). R-Gel localization in cells is confirmed by comparing and superimposing the fluorescence image and the visible light image (transmitted light image).

The obtained cells in the dish were observed using a confocal laser microscope (Nikon EZ-C1). It was found that Cy2-R-Gel was incorporated into tubular epithelial cells (FIG. 13). In addition, a Cy2-R-Gel incorporation experiment was conducted with the addition of lysozyme which is known to competitively inhibit incorporation via megalin receptors of tubular epithelial cells when added. As a result, incorporation of Cy2-R-Gel was inhibited.

Accordingly, it was also revealed that the affected kidney-targeting agent provided with R-Gel is incorporated into tubular epithelial cells. Renal cell cancer is a malignant carcinoma formed through malignant alteration of kidney tissue cells, and in particular, tubular epithelial cells. In view of this, it is understood that incorporation of R-Gel into tubular epithelial cells indicates that R-Gel is very useful for a targeting agent for a kidney affected with renal cell cancer.

(14) Cell Incorporation Experiment Using Inflammatory Cells/Peritoneal Macrophages Accumulation of R-Gel in an inflammatory kidney was demonstrated in vivo in animals. Next, interaction between R-Gel and macrophages (M cells) (inflammatory cells) was examined for elucidation of the R-Gel accumulation mechanism.

In order to examine whether or not R-Gel would interact with Mφ cells or would be incorporated by Mφ cells, an in vitro experiment was carried out to examine incorporation by Mφ cells. The Mφ cells used herein were mouse peritoneal Mφ cells. Cy2-labeled R-Gel was added to Mφ cells collected from the mouse peritoneal tissue, followed by incubation at 37° C. for 3 hours. Then, the cells were observed using a confocal laser microscope.

Six-week-old male DDY mice were used. 3% thioglycolate (2 mL) was peritoneally administered thereto. Peritoneal Mφ cells were collected from each mouse 3 days after the administration. Upon cell collection, RPMI1640 was used as a medium and 10% FBS (final concentration) was used as serum. Then, 50 μg/mL serum-free Cy2-R-Gel (final concentration) was added to the collected and cultured Mφ cells, followed by incubation at 37° C. for 3 hours, followed by observation by a confocal laser microscope.

Figure 14:
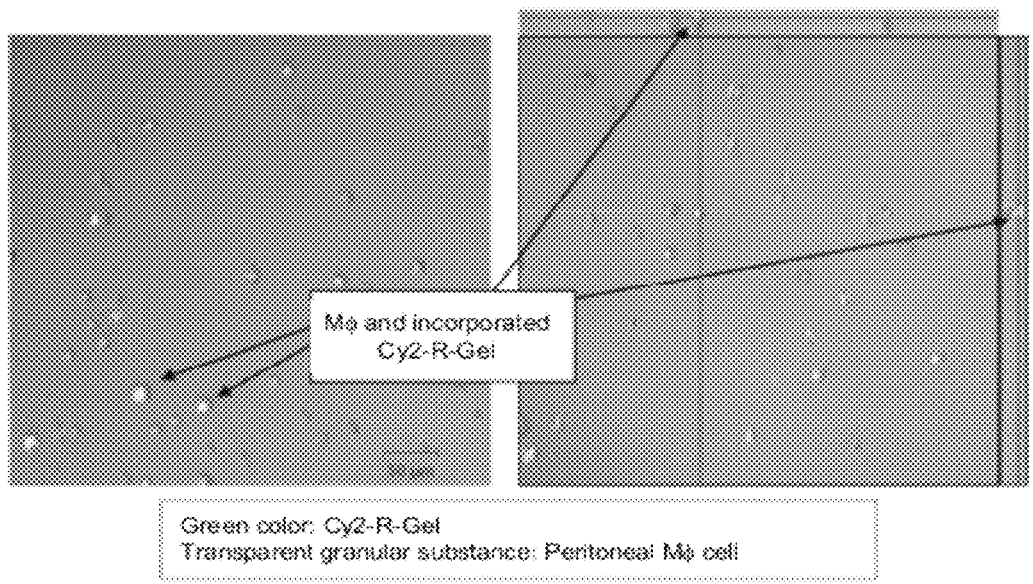
FIG. 14 shows results of a cell incorporation test using inflammatory cells/peritoneal macrophages.

As a result, localization of fluorescence signals of Cy2-R-Gel in peritoneal Mφ cells was observed (FIG. 14). This indicated incorporation of R-Gel by peritoneal Mφ cells. Accordingly, it was shown that the affected kidney-targeting agent provided with R-Gel is incorporated into inflammatory cells which increase in inflammatory legions. Thus, the results obtained by in vitro experiments suggested a reason for why R-Gel accumulates in an affected kidney to a greater extent than in a normal kidney.

---

The invention claimed is:

1. A method for imaging, specifically, a kidney affected with a disease, which comprises:
administering, to a subject, a kidney-imaging agent, to thereby deliver the kidney-imaging agent specifically to the kidney affected with the disease, wherein said kidney-imaging agent is a recombinant gelatin labeled with a probe, wherein the recombinant gelatin is not crosslinked, and said kidney imaging agent is dissolved in a liquid, and
imaging the kidney by means of the labeled probe,
wherein the recombinant gelatin has the following (1) or (2):
(1) the amino acid sequence shown in SEQ ID NO: 1; or
(2) an amino acid sequence having 80% or more homology to the amino acid sequence shown in SEQ ID NO: 1 and having an action to accumulate in kidney,
and wherein the disease is acute nephritis, interstitial nephritis, glomerulonephritis, IgA nephropathy, or renal failure by ischemia-reperfusion.

2. The method of claim 1, wherein the recombinant gelatin comprises repeats of a sequence represented by Gly-X-Y characteristic to collagen and has a molecular weight of 2 KDa to 100 KDa, wherein X and Y each independently represents an amino acid and the plurality of Gly-X-Y sequences may be the same or different.

3. The method of claim 1, wherein the recombinant gelatin comprises repeats of a sequence represented by Gly-X-Y characteristic to collagen and has a molecular weight of 10 KDa to 90 KDa, wherein X and Y each independently represents an amino acid and the plurality of Gly-X-Y sequences may be the same or different.

4. The method of claim 1, wherein the recombinant gelatin comprises repeats of a sequence represented by Gly-X-Y characteristic to collagen and has two or more sequences of a cell adhesion signal in a single molecule, wherein X and Y each independently represents an amino acid and the plurality of Gly-X-Y sequences may be the same or different, and wherein the cell adhesion signal sequence is an amino acid sequence represented by Arg-Gly-Asp.

5. The method of claim 1, wherein the amino acid sequence of the recombinant gelatin does not comprise any of serine and threonine.

6. The method of claim 1, wherein the amino acid sequence of the recombinant gelatin does not comprise an amino acid sequence represented by Asp-Arg-Gly-Asp (SEQ ID NO: 2).

7. The method of claim 1, wherein the recombinant gelatin is represented by the following formula:

A-[(Gly-X-Y)$_n$]$_m$—B wherein A represents any amino acid or amino acid sequence, B represents any amino acid or amino acid sequence, there exist n amino acids each independently represented by X, there exist n amino acids each independently represented by Y, n represents an integer from 3 to 100, m represents an integer of 2 to 10, X and Y each independently represents an amino acid, and n Gly-X-Y sequences may be the same or different.

8. The method of claim 1, wherein the recombinant gelatin is represented by the following formula:

Gly-Ala-Pro-[(Gly-X-Y)$_{63}$]$_3$-Gly wherein there exist 63 amino acids each independently represented by X, there exist 63 amino acids each independently represented by Y, X and Y independently represents an amino acid, and 63 Gly-X-Y sequences may be the same or different.

9. The method of claim 1, wherein the labeled probe is a fluorescent dye, a radioisotope, a nuclide used for PET, a nuclide used for SPECT, an MRI contrast medium, a CT contrast medium, or a magnetic material.

10. The method of claim 9, wherein the fluorescent dye is a quantum dot, indocyanine green, or a near-infrared fluorescent dye; each of the radioisotope, the nuclide used for PET, and the nuclide used for SPECT is $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$CU, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{186/188}$Re, $^{125}$I, or a complex thereof, or a combination thereof; and each of the MRI contrast medium, the CT contrast medium, and the magnetic material is gadolinium, Gd-DTPA, Gd-DTPA- BMA, Gd-HP-DO3A, iodine, iron, iron oxide, chromium, manganese, a complex or chelate complex thereof, or a combination thereof.

11. The method of claim 1, wherein the recombinant gelatin and the labeled probe are physically or chemically bound directly or via a linker.

12. The method of claim 11, wherein the bond is a coordinate bond, a covalent bond, a hydrogen bond, a hydrophobic interaction or a physical adsorption.

* * * * *

SEQUENCE LISTING

```
<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic polypeptide

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285
```

```
Gly Ala Ala Gly Leu Pro Gly Pro Lys Gly Glu Arg Gly Asp Ala Gly
        290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
            325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
            405                 410                 415

Lys Gly Ala Asp Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
        435                 440                 445

Asp Ala Gly Pro Lys Gly Ala Asp Gly Ala Pro Gly Lys Asp Gly Val
450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
            485                 490                 495

Ala Asp Gly Ala Pro Gly Lys Asp Gly Val Arg Gly Leu Ala Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
        530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
            565                 570

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 2

Asp Arg Gly Asp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Arg Glu Asp Val
```

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 4

Tyr Ile Gly Ser Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 5

Pro Asp Ser Gly Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 6

Arg Tyr Val Val Leu Pro Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 7

Leu Gly Thr Ile Pro Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 8

Arg Asn Ile Ala Glu Ile Ile Lys Asp Ile
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 9

Ile Lys Val Ala Val
1               5

```
<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 10

Asp Gly Glu Ala
1

<210> SEQ ID NO 11
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 11

Glu Arg Gly Asp
1
```